United States Patent [19]

Ono et al.

[11] Patent Number: 4,966,982
[45] Date of Patent: Oct. 30, 1990

[54] PROCESS FOR THE PRODUCTION OF LACTIDE

[75] Inventors: Hiroshi Ono, Fujisawa; Heng Phala, Yokohama, both of Japan

[73] Assignee: Mitsui Toatsu Chemicals, Incorporated, Tokyo, Japan

[21] Appl. No.: 343,448

[22] Filed: Apr. 26, 1989

[30] Foreign Application Priority Data

Apr. 27, 1988 [JP] Japan .................... 63-102756

[51] Int. Cl.$^5$ ........................... C07D 319/10
[52] U.S. Cl. .................................. 549/274
[58] Field of Search .......................... 549/274

[56] References Cited

U.S. PATENT DOCUMENTS

| 3,763,190 | 10/1973 | Ross et al. | 549/274 |
| 3,960,152 | 6/1976 | Augurt et al. | 128/335.5 |
| 4,033,938 | 4/1977 | Augurt et al. | 549/274 |
| 4,835,293 | 5/1989 | Bhatia | 549/274 |

FOREIGN PATENT DOCUMENTS

| 0264926 | 4/1988 | European Pat. Off. | 547/274 |
| 1122229 | 6/1968 | United Kingdom . | |

OTHER PUBLICATIONS

A. Sporzyuski et al., "A New Method of Preparing Glycollide," in Recueil, vol. 68, Nos. 9/10, Sep./Oct. 1949, pp. 613 to 618.

Chujo et al., "Ring-Opening Polymerization of Glycolide" in Die Makromolekulare Chemie, vol. 100, 1967, pp. 262–266.

*Primary Examiner*—Richard L. Raymond
*Assistant Examiner*—Mark W. Russell
*Attorney, Agent, or Firm*—Fisher, Christen & Sabol

[57] ABSTRACT

Disclosed is a process for the production of highly pure lactide, especially having a sufficiently high purity to be usable as a raw material for the synthesis of polymers, by heating a 2-halopropionate in a non-aqueous solvent.

13 Claims, No Drawings

PROCESS FOR THE PRODUCTION OF LACTIDE

BACKGROUND OF THE INVENTION

1. Field of the Invention

This invention relates to a process for the production of lactide in which highly pure lactide usable as a raw material for the synthesis of a polyacetic lactic acid can be industrially produced at low cost.

Although highly pure lactide has heretofore been produced by using lactic acid as the starting material, a salt of a 2-halopropionic acid is used in place of lactic acid in the process of the present invention.

2. Description of the Prior Art

Usually, lactide is produced by heating lactic acid at about 200° C. at a pressure of 20 mmHg or less to condense it with the elimination of water. Since readily obtainable lactic acid is used as the starting material, this process is often employed to synthesize a labo-use amount of lactide. However, this process must be carried out in a relatively high vacuum and, moreover, the reaction rate is low. Accordingly, high equipment costs will be required in order to carry out this process on an industrial scale. Furthermore, highly pure lactic acid will be required in order to produce highly pure lactide according to this process. A high degree of purification of lactic acid, in turn, will require considerable purification costs. For these reasons, it has been difficult to produce lactide of polymer grade industrially at low cost.

SUMMARY OF THE INVENTION

We have made a detailed study of the production of lactide with a view to developing a process by which lactide having a sufficiently high purity to be usable as a raw material for the synthesis of a polylactic acid is produced. As a result, we have found that an alkali metal or alkaline earth metal salt of a halopropionic acid can be converted into lactide by heating the salt in a non-aqueous solvent. The present invention has been completed on the basis of this finding.

According to the present invention, there is provided a process for the production of lactide which comprises the steps of heating an alkali metal or alkaline earth metal salt of a 2-halopropionic acid in a non-aqueous solvent to convert the salt into lactide, and separating the lactide so formed.

More specifically, the present invention relates to a novel process for producing lactide according to the following equation (1) or (2):

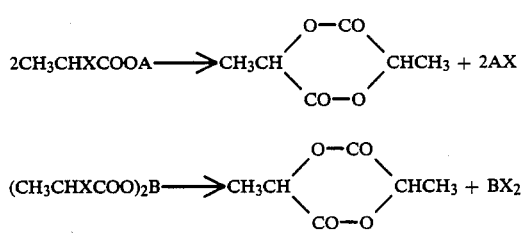

wherein A is an alkali metal, B is an alkaline earth metal, and X is a halogen atom. The lactide thus obtained is a compound useful as a raw material for the synthesis of a polylactic acid.

DETAILED DESCRIPTION OF THE INVENTION

The term "2-halopropionic acid" as used herein comprehends 2-chloropropionic acid, 2-bromopropionic acid and 2-iodopropionic acid. Among them, 2-chloropropionic acid is preferably used in the process of the present invention because it is most readily obtainable in industry and suitable for the intended purpose of the present invention.

Alkali metal or alkaline earth metal salts of such 2-halopropionic acids can readily be prepared by reacting a 2-halopropionic acid with an alkali metal such as lithium, sodium, potassium, rubidium or cesium; an alkaline earth metal such as magnesium, calcium, strontium or barium; or an oxide, hydroxide or weak acid salt of an alkali metal or alkaline earth metal, such as calcium oxide, strontium oxide, magnesium oxide, sodium oxide, lithium hydroxide, sodium hydroxide, potassium hydroxide, rubidium hydroxide, cesium hydroxide, calcium hydroxide, barium hydroxide, lithium carbonate, sodium carbonate, potassium carbonate, calcium carbonate, strontium carbonate, barium carbonate, sodium hydrogencarbonate or potassium hydrogencarbonate.

Specific examples of the alkali metal or alkaline earth metal salts of 2-halopropionic acids prepared from the above-described materials include alkali metal or alkaline earth metal salts of 2-chloropropionic acid, such as lithium 2-chloropropionate, sodium 2-chloropropionate, potassium 2-chloropropionate, rubidium 2-chloropropionate, cesium 2-chloropropionate, magnesium 2-chloropropionate, calcium 2-chloropropionate, strontium 2-chloropropionate and barium 2-chloropropionate; alkali metal or alkaline earth metal salts of 2-bromopropionic acid, such as lithium 2-bromopropionate, sodium 2-bromopropionate, potassium 2-bromopropionate, rubidium 2-bromopropionate, cesium 2-bromopropionate, magnesium 2-bromopropionate, calcium 2-bromopropionate, strontium 2-bromopropionate and barium 2-bromopropionate; alkali metal or alkaline earth metal salts of 2-iodopropionic acid, such as lithium 2-iodopropionate, sodium 2-iodopropionate, potassium 2-iodopropionate, rubidium 2-iodopropionate, cesium 2-iodopropionate, magnesium 2-iodopropionate, calcium 2-iodopropionate, strontium 2-iodopropionate and barium 2-iodopropionate.

Since these 2-halopropionic acid salts can readily be purified by such techniques as recrystallization, the purity of the resulting lactide can be enhanced by purifying the 2-halopropionic acid salt used as the starting material.

When these salts are synthesized or purified by recrystallization, water may be used as the solvent. However, in order to obtain the salts in the form of crystals, low-boiling alcohols, ketones, esters, ethers and the like are preferably used. Among them, low-boiling alcohols such as methanol, ethanol and isopropyl alcohol are especially preferred.

The non-aqueous solvent used in the process of the present invention must be one which can dissolve at least a part of the alkali metal or alkaline earth metal salt of 2-halopropionic acid under reaction conditions and does not react with lactide to reduce the yield thereof. In particular, non-aqueous solvents having a low-boiling point, a high solubility for lactide and a low solubility for alkali metal or alkaline earth metal halides are preferred for the purpose of obtaining a highly pure form of lactide.

Such solvents include, for example, ketones, esters and ethers. Specific examples of preferred solvents are acetone, methyl ethyl ketone, methyl isobutyl ketone, isopropyl acetate, diethyl ether, dioxane and tetrahydrofuran.

Among these solvents, ketones such as acetone, methyl ethyl ketone and methyl isobutyl ketone are especially preferred.

In carrying out the process of the present invention, an alkali metal or alkaline earth metal salt of 2-halopropionic acid is dissolved in the above-defined non-aqueous solvent which has been heated to a temperature in the range of 100° to 250° C.

The solvents preferably used in the process of the present invention have a relatively high vapor pressure in the above-described temperature range. Accordingly, the process of the present invention is preferably carried out under pressure, especially in the vicinity of the pressure produced by the solvent itself at the reaction temperature.

Under these temperature and pressure conditions, the reaction time usually ranges from 0.1 to 6 hours and preferably from 0.5 to 2 hours, though it may vary according to the reaction temperature.

Another advantage of the present invention is that the lactide obtained in the above-described manner can readily be purified by recrystallization to yield a purer form of lactide. This is due to the fact that the greater part of the impurities which may present in the lactide produced according to the process of the present invention comprises unreacted o-halopropionate and this impurity can readily be removed by recrystallization. Preferred examples of solvents usable for the recrystallization of lactide include ketones, esters, ethers and alcohols. Among them, acetone, methyl ethyl ketone, methyl isobutyl ketone, methyl acetate, ethyl acetate, isopropyl acetate, diethyl ether and the like are especially preferred because they are easy to handle and can yield lactide having a relatively high purity.

The present invention is further illustrated by the following examples.

REFERENCE EXAMPLE 1

Preparation of sodium 2-chloropropionate 108.5 g (1 mole) of 2-chloropropionic acid was dissolved in 1,000 ml of methanol, and the resulting solution was neutralized by adding a (ca. 1N) methanol solution of sodium hydroxide dropwise thereto. Thus, there was obtained a methanol solution of sodium 2chloropropionate Then, the above solution was evaporated at about 50° C under reduced pressure until all of the methanol was removed. Thus, there was obtained about 130 g of sodium 2-chloropropionate in the form of crystals.

EXAMPLE 1

10 g of the sodium 2-chloropropionate prepared according to the procedure of Reference Example 1 was dispersed in 100 ml of acetone, and the resulting suspension was heated in an autoclave at 200° C for 2 hours. During this process, the pressure within the autoclave was maintained at about 25 atmospheres. After the autoclave was cooled to room temperature, the lid was opened and the reaction mixture was taken out. Since the reaction mixture consisted of a liquid phase (acetone layer) and a solid (sodium chloride), the solid was removed by filtration and the acetone layer was concentrated by vacuum distillation (at 40° C.) to obtain about 6 g of crude lactide in the form of crystals. When a sample of the lactide was hydrolyzed and then analyzed by acid-base titration, its yield was found to be 76% based on the amount of sodium 2-chloropropionate used as the starting material. Then, this crude lactide was recrystallized from an ethyl acetate solution to obtain about 1.7 g of purified lactide having a purity of 99.7% or higher.

EXAMPLE 2

Potassium 2-chloropropionate was prepared in the same manner as described in Reference Example 1, except that potassium hydroxide was used in place of the sodium hydroxide.

In the same manner as described in Example 1, the above potassium 2-chloropropionate was heated in acetone at 190° C. for 1.5 hours to obtain about 4 g of crude lactide in the form of crystals. In this case, the yield of lactide was found to be 78% based on the amount of potassium 2-chloropropionate used as the starting material. When this crude lactide was recrystallized in the same manner as described in Example 1, there was obtained 1.3 g of purified lactide having a purity of 99.7% or higher.

REFERENCE EXAMPLE 2

Preparation of calcium 2-chloropropionate 108.5 g (1 mole) of 2-chloropropionic acid was dissolved in 1,000 ml of ethanol. To the resulting solution was slowly added about 28 g (0.5 mole) of calcium oxide which had been finely ground in dry air. This mixture was stirred in a warm water bath at about 50° C. until the calcium oxide dissolved completely.

Then, using a rotary evaporator, the above solution was evaporated at 50° C. under slightly reduced pressure until all of the ethanol was removed. Thus, there was obtained about 128 g of calcium 2-chloropropionate in the form of crystals.

EXAMPLE 3

10 g of the calcium 2-chloropropionate prepared according to the procedure of Reference Example 2 was dispersed in about 100 ml of dioxane, and the resulting dispersion was heated in an autoclave at 180° C. for 1 hour to effect reaction.

After completion of the reaction, the presence of lactide in the reaction product mixture was confirmed by comparing its infrared absorption spectrum with that of a standard sample.

EXAMPLE 4

Barium 2-chloropropionate was prepared in the same manner as described in Reference Example 2, except that 99 g of barium carbonate was used in place of the calcium oxide.

Then, the barium 2-chloropropionate thus-obtained was reacted in the same manner as described in Example 3. The formation of lactide was confirmed in the same manner as described above.

REFERENCE EXAMPLE 3

Preparation of sodium 2-bromopropionate

Sodium 2-bromopropionate was prepared in the same manner as described in Reference Example 1, except that the same molar amount of 2-bromopropionic acid was used in place of the 2-chloropropionic acid.

EXAMPLE 5

10 g of the sodium 2-bromopropionate prepared in Reference Example 3 was dispersed in 100 ml of methyl ethyl ketone, and the resulting dispersion was heated in an autoclave at 160° C. for 0.5 hour to effect reaction.

After completion of the reaction, the presence of lactide in the reaction product mixture was confirmed by examining its infrared absorption spectrum.

REFERENCE EXAMPLE 4

Preparation of sodium 2-iodopropionate

Sodium 2-iodopropionate was prepared in the same manner as described in Reference Example 1, except that the same molar amount of 2-iodopropionic acid was used in place of the 2-chloropropionic acid.

EXAMPLE 6

10 g of the sodium 2-iodopropionate prepared in Reference Example 4 was dispersed in 100 ml of methyl isobutyl ketone, and the resulting dispersion was heated in an autoclave at 140° C. for 1 hour to effect reaction.

After completion of the reaction, the presence of lactide in the reaction product mixture was confirmed by examining its infrared absorption spectrum as described previously.

We claim:

1. A process for the formation of a lactide, comprising the step of heating an alkali metal or alkaline earth metal salt of a 2-halopropionic acid in a non-aqueous solvent which has a low boiling point, which has a high solubility for the lactide and which has a low solubility for alkali metal or alkaline earth metal halides, at a reaction temperature of 100° to 250° C. and in the vicinity of a pressure produced by the solvent itself at the reaction temperature to convert the salt into the lactide 2. The process as claimed in claim 1 wherein the non-aqueous solvent is one member selected from the group consisting of Ketones, esters and ethers.

3. The process as claimed in claim 1 wherein the non-aqueous solvent is one member selected from the group consisting of acetone, methyl ethyl ketone, methyl isobutyl ketone, isopropyl acetate, diethyl ether, dioxane and tetrahydrofuran.

4. The process as claimed in claim 1 wherein the non-aqueous solvent is a Ketone selected from the group consisting of acetone, methyl ethyl ketone and methyl isobutyl ketone.

5. The process as claimed in claim 1 wherein the 2-halopropionic acid is 2-chloropropionic acid.

6. The process as claimed in claim 1 wherein the alkali metal salt of the 2-halopropionic acid is the sodium salt of the 2-halopropionic acid.

7. The process as claimed in claim 1 wherein the alkali metal salt of the 2-halopropionic acid is the potassium salt of the 2-halopropionic acid.

8. The process as claimed in claim 1 wherein the alkaline earth metal salt of the 2-halopropionic acid is the calcium salt of the 2-halopropionic acid.

9. The process as claimed in claim 1 wherein the alkaline earth metal salt of the 2-halopropionic acid is the barium salt of the 2-halopropionic acid.

10. The process as claimed in claim 1 wherein the lactide is separated from the reaction product mixture.

11. The process as claimed in claim 10 wherein the lactide is separated by removing a solid phase from the reaction product mixture to obtain a liquid phase and then evaporating the non-aqueous solvent from the liquid phase.

12. A process for producing a lactide, comprising the step of heating an alkali metal or alkaline earth metal salt of a 2-halopropionic acid in a non-aqueous solvent selected from the group consisting of acetone, methyl ethyl ketone, methyl isobutyl ketone and dioxane at a reaction temperature of 140° to 200° C., in the vicinity of an autogenous pressure of the solvent at the reaction temperature.

13. The process as claimed in claim 12 wherein the autogenous pressure is about 25 atmospheres.

* * * * *